(12) United States Patent
Schulz

(10) Patent No.: US 6,795,193 B2
(45) Date of Patent: Sep. 21, 2004

(54) SCATTEROMETER INCLUDING AN INTERNAL CALIBRATION SYSTEM

(75) Inventor: Bernd Schulz, Radebeul (DE)

(73) Assignee: Advanced Micro Devices, Inc., Austin, TX (US)

( * ) Notice: Subject to any disclaimer, the term of this patent is extended or adjusted under 35 U.S.C. 154(b) by 4 days.

(21) Appl. No.: 10/304,572

(22) Filed: Nov. 26, 2002

(65) Prior Publication Data

US 2003/0223072 A1 Dec. 4, 2003

(30) Foreign Application Priority Data

May 31, 2002 (DE) ........................................ 102 24 162

(51) Int. Cl.⁷ .............................................. G01N 21/55
(52) U.S. Cl. ...................................................... 356/445
(58) Field of Search ................................ 356/445–448, 356/237.1–237.5, 244; 250/306, 307, 310, 311, 252.1, 372

(56) References Cited

U.S. PATENT DOCUMENTS

| | | | |
|---|---|---|---|
| 5,486,701 A * | 1/1996 | Norton et al. ............... 250/372 |
| 5,867,276 A | 2/1999 | McNeil et al. .............. 356/445 |
| 5,877,860 A | 3/1999 | Borden ....................... 356/376 |
| 5,880,838 A | 3/1999 | Marx et al. .................. 356/351 |
| 6,051,348 A | 4/2000 | Marinaro et al. ............. 430/30 |
| 6,081,334 A | 6/2000 | Grimbergen et al. ........ 356/357 |
| 6,245,584 B1 | 6/2001 | Marinaro et al. ............. 438/14 |
| 6,433,878 B1 | 8/2002 | Niu et al. .................... 356/603 |
| 2002/0135781 A1 | 9/2002 | Singh et al. ................. 356/601 |
| 2002/0159054 A1 * | 10/2002 | Ebert et al. .................. 356/244 |
| 2003/0147070 A1 * | 8/2003 | Sezginer et al. .......... 356/237.2 |
| 2003/0193666 A1 * | 10/2003 | Abraham et al. ......... 356/237.4 |

* cited by examiner

*Primary Examiner*—Michael P. Stafira
(74) *Attorney, Agent, or Firm*—Williams, Morgan & Amerson, P.C.

(57) ABSTRACT

A scatterometer system comprises a pitch calibration station that allows the monitoring of a tool status of the scatterometry system without involving a user's interaction. The pitch calibration station comprises a pitch calibration standard, for example in the form of a grid pattern that may conveniently be evaluated on the basis of a reference data library. By providing the pitch calibration station, the measurement process may easily be adapted to include reference measurements on a regular basis so as to increase the reliability of measurement values obtained by scatterometry. In one particular example, a corresponding set of instructions for performing the calibration measurement may be implemented into a self-test routine of the scatterometry system.

27 Claims, 3 Drawing Sheets

SCATTEROMETER INCLUDING AN INTERNAL CALIBRATION SYSTEM

BACKGROUND OF THE INVENTION

1. Field of the Invention

Generally, the present invention relates to the field of metrology and metrology tools used in the fabrication of integrated circuits, and, more particularly, to optical measurement tools and methods for determining characteristics of circuit elements during the various manufacturing stages.

2. Description of the Related Art

The manufacturing of integrated circuits requires the formation and interconnection of a huge number of individual circuit elements, such as transistors, capacitors, resistors and the like, on a small chip area. In producing the circuit elements, a plurality of material layers are successively deposited on a substrate and they are patterned in accordance with design requirements by sophisticated photolithographic and etch techniques. As the dimensions of the individual circuit elements decrease and the complexity of the circuit increases with every new generation of integrated circuits, tolerances for the individual process steps involved in fabricating the circuits have to be maintained within very strictly set ranges. In order to monitor process quality during the various manufacturing stages, great efforts are made to provide measurement results representing the effect and the quantity of the individual process steps in the most efficient manner possible. Consequently, a plurality of measurement tools, also referred to as metrology tools, are provided as part of, or separate from, the process line to allow the adjustment or readjustment of process parameters to form the circuit elements meeting the specification set by the design rules. Among the measurement methods used to determine the characteristics of circuit features, those techniques which allow the gathering of highly precise measurement results in a non-destructive manner are gaining in importance. For example, in many situations, the exact determination of a layer thickness is essential and a plurality of metrology tools have been developed for this task. Among others, so-called spectroscopic ellipsometers or photometers are preferably used to provide a light beam of specified optical characteristics and to detect a secondary light beam reflected by a substrate bearing the material layer, the thickness of which is to be determined, to obtain the required information. Recently, such optical metrology tools have also been used to determine properties of circuit features patterned in a material layer. To this end, a periodic structure of test features is formed at a specified location on the substrate and is exposed to a light beam of known optical characteristics.

In this context, it should be noted that the terms "optical" and "light beam" refer to any type of radiation, e.g., microwaves, infrared light, visible light, x-rays and even charged particles, having an appropriate wavelength so as to carry information on the periodic structure upon being scattered therefrom.

A detector is positioned to receive the light beam scattered by the periodic structure to obtain measurement spectra, from which information related to the periodic structure may be extracted. Many types of apparatus may be used for providing an appropriate light beam and for detecting the diffracted beam. For example, U.S. Pat. No. 5,867,276 describes a so-called 2-θ-Scatterometer, wherein the angle of incidence of a light beam is continuously varied by synchronously rotating the sample and the detector. Additionally, this document describes a scatterometer system utilizing a rotating block to translate a light beam emitted from a light source to different points of the entrance aperture of a lens to illuminate the substrate at different angles of incidence. Moreover, this document describes a scatterometer with a fixed angle of incidence utilizing a multi-wavelength illumination source to create and obtain the required information from the diffracted multi-wavelength beam. From the information contained in the measurement spectrum, the optical and dimensional properties of individual elements that form the periodic structure and the thickness of underlying films may be extracted, for example, by statistical techniques. The parameters of interest of the periodic structure may include the width of lines, if the periodic structure contains lines and spaces, the sidewall angles, and other structural details.

In principle, information indicative of values of these parameters may be extracted by computing an intensity distribution of the scattered beam with respect to wavelength, location in space, polarization, and the like from the basic design of the periodic structure, the optical characteristics of the materials of which the periodic structure is formed, and from the basic physical equations (Maxwell's equations) describing the interaction of the radiation with matter. The results, obtained by computation, may then be compared to actual measurement data and the difference between the two sets of data is indicative of a variation of one or more parameters. For instance, a deviation of the sidewall angle of a line within a grid pattern may lead to a subtle intensity variation compared to the computed spectrum, and the difference in intensity may then be assigned to a specific value of the sidewall angle. The computation of a corresponding set of reference spectra, however, requires a fairly large amount of computational power and computation time and thus, commonly, computing the reference data is carried out in advance and reference spectra or data for a given type of periodic structure are stored in a so-called library.

In addition to the scatterometers described above, metrology tools that allow an optical measurement of layer thickness, such as spectroscopic ellipsometers and photometers, are used more frequently for scatterometry due to their broad availability. In order to reliably obtain precise film thickness measurement results, the properties of these metrology tools have to be continuously monitored and maintained within very strict margins, since a very subtle variation, for instance, of the light source and/or the detector, may result in an intolerable degradation of measurement performance. Thus, automatic measurement cycles are commonly carried out on a regular basis with internal film thickness standards to monitor and possibly readjust the metrology tool. Thus, when used for scatterometry, any re-calibration and/or readjustment and/or drift of the hardware of the tool may also affect measurement results of the scatterometry measurement, although, in principle, the scatterometry results may be considered as "absolute," since they are obtained on the basis of the fundamental physical equations. The effect of any hardware variation of the metrology tool on scatterometry results is therefore conventionally monitored by periodically measuring a set of reference wafers, which are also referred to as "golden wafers." The verification of the current hardware adjustment of the tool, therefore, periodically requires a user's attention and time to substantially avoid any hardware drift that may jeopardize the reliability of scatterometric measurement.

In view of the above situation, there exists a need for reliably monitoring the status of metrology tools used for scatterometry in a time-efficient and effective manner.

SUMMARY OF THE INVENTION

Generally, the present invention is directed to apparatus and methods used in scatterometry, wherein a pitch calibration standard, i.e., a simple periodic standard pattern and a corresponding reference data library, is integrated into the metrology tool so that any variations in the hardware of the tool may be detected and monitored in a time-efficient manner.

According to one illustrative embodiment of the present invention, a scatterometer system comprises a light source configured to emit a light beam of predefined optical characteristics and a detector configured to receive a light beam scattered by a sample. Moreover, a substrate holder is provided that is adapted to receive the sample and hold it in place during a measurement cycle. Additionally, the scatterometer system comprises a pitch calibration station including a pitch calibration standard and a library data unit adapted to provide reference data indicative of the pitch calibration standard.

According to still a further illustrative embodiment of the present invention, a method of calibrating a scatterometer comprises providing a pitch calibration standard and establishing a reference data library for the pitch calibration standard. Moreover, measurement data of the pitch calibration standard is obtained and is compared with the reference data library.

In yet a further illustrative embodiment of the present invention, a method of operating a scatterometer comprises starting a self-test routine of the scatterometer. The self-test routine comprises obtaining measurement data from a pitch calibration standard and comparing the measurement data with reference data of the pitch calibration standard. The scatterometer is released for further measurement when a result of the comparison is within a predefined allowable range.

BRIEF DESCRIPTION OF THE DRAWINGS

The invention may be understood by reference to the following description taken in conjunction with the accompanying drawings, in which like reference numerals identify like elements, and in which.

Figure 1A:
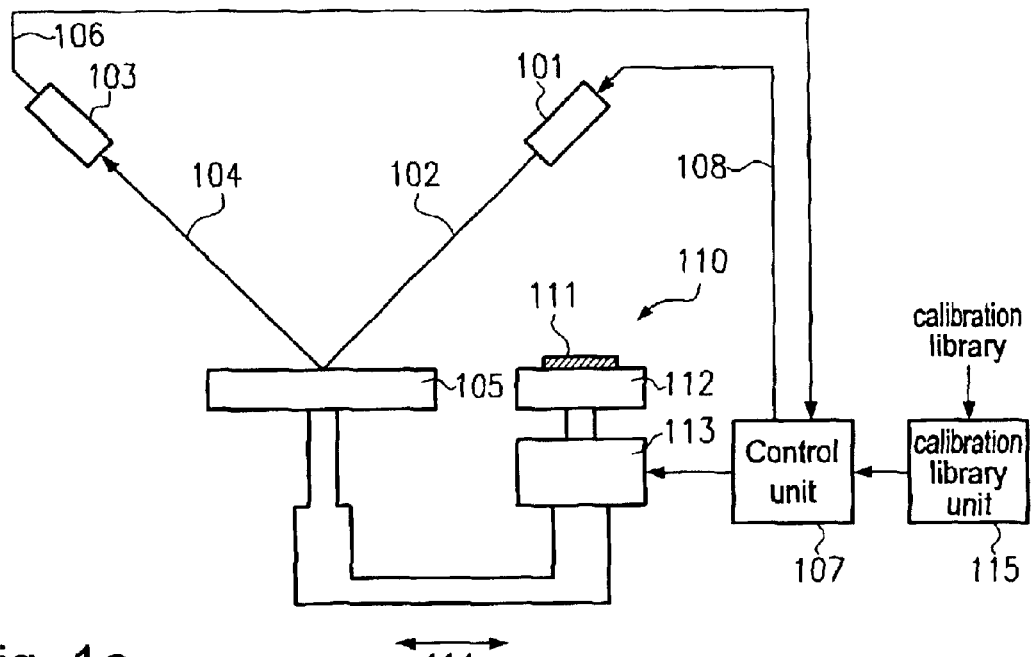
FIGS. 1a–1c schematically show simplified arrangements of scatterometry systems in accordance with illustrative embodiments of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In the following detailed description, reference is made to scatterometer systems including a spectroscopic ellipsometer as a light source, a detector and a substrate holder. However, the basic concept of the present invention, i.e., the provision of a system-inherent pitch calibration station, may be applied to any appropriate measurement tool especially designed and configured for scatterometry measurements, irrespective of whether the measurement tool is a stand-alone device or integrated in an already available process tool.

Figure 1B:
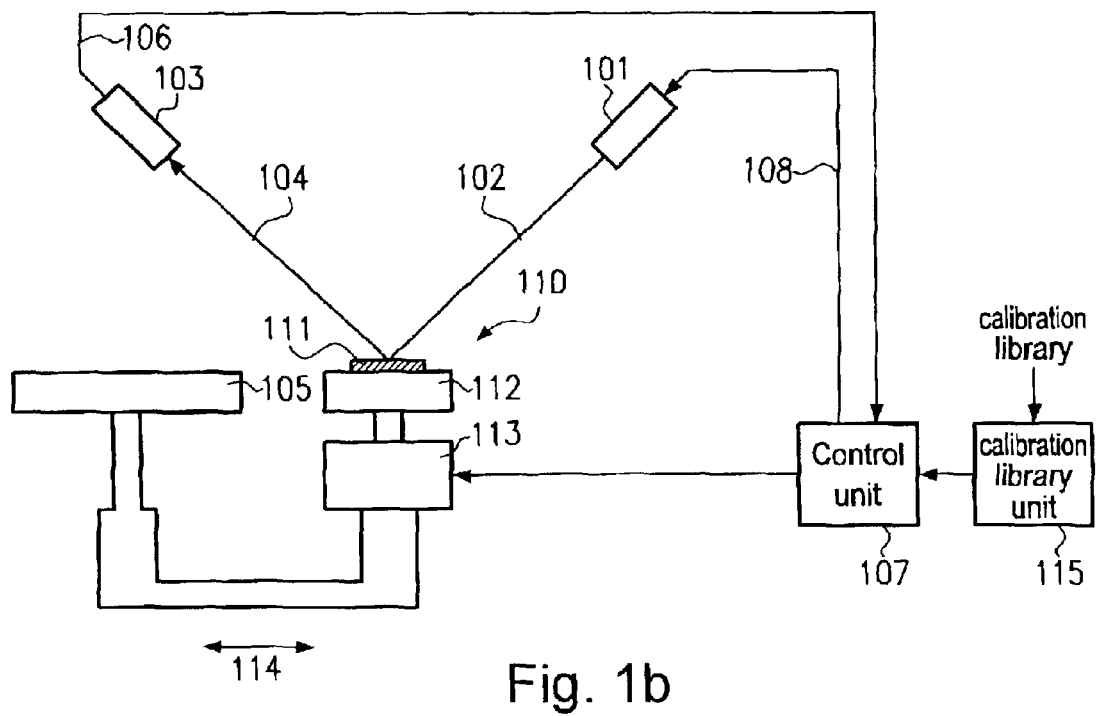
Figure 1C:
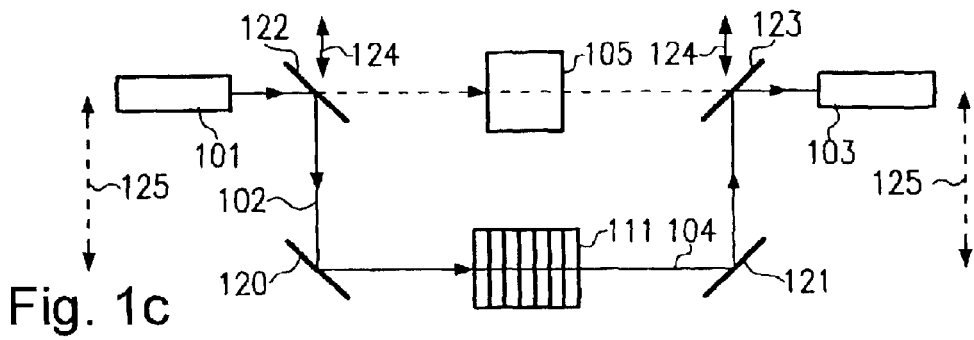

With reference to FIGS. 1a–1c, basic arrangements of metrology tools including a pitch calibration station will be illustrated and described in a schematic and simplified manner. In FIG. 1a, a scatterometry system 100 includes a light source 101 that is configured to emit a light beam 102 of predefined optical characteristics. As previously explained, the "light source" 101 may be any appropriate source of radiation that may be used in providing the light beam 102 such that properties of interest on a periodic structure may be resolved by the light beam 102. To this end, the light source 101 may include any optical system (not shown) to provide the radiation emitted by the light source 101 with the required characteristics. For example, the light source 101 may be adapted to provide a linearly polarized light beam 102 with varying wavelength in the range of approximately 200–1000 nm. The system 100 further comprises a detector 103 that is adapted and arranged to receive a light beam 104 scattered and reflected by a substrate (not shown) mounted on a substrate holder 105. The detector 103 is also configured to provide an output signal 106 indicative of at least a portion of the optical characteristics of the received light beam 104. The light source 101 and the detector 103 may be connected to a control unit 107 that may be configured to receive the output signal 106 and to supply a control signal to the light source 101 via a communication line 108. The system 100 further comprises a pitch calibration station 110 including a pitch calibration standard 111 that may be removably attached to a substrate stage 112, which, in turn, may be mounted on a drive assembly 113. The drive assembly 113 is adapted to provide translational (in three directions) and rotational movement of the substrate stage 112, and the calibration standard 111 positioned thereon. Such movement may be provided by various electromechanical systems, e.g., gears, motors, etc., that are configured in such a manner so as to produce the desired translational and rotational movement. The pitch calibration standard 111 may be made of any appropriate substrate including a periodic structure suitable for a scatterometry measurement. In some embodiments, the pitch calibration standard 111 may be a grid pattern formed on and/or in a substrate, such as a silicon substrate with a predefined pitch between lines and spaces in the range of approximately 0.1–1 $\mu$m. Appropriate forms of the pitch calibration standard 111 are Hitachi Standard Microscale HJ-1200 (traceable) and VLSI NanoLattice(TM) Standard.

In one embodiment, as depicted in FIGS. 1a and 1b, the pitch calibration station 110 may be mechanically coupled to the substrate holder 105, such that the pitch calibration station 110 and the substrate holder 105 are moveable in a direction as indicated by arrow 114. In this way, either the substrate holder 105 (FIG. 1a) or the pitch calibration station 110 (FIG. 1b) may be positioned to receive the light beam 102. The pitch calibration station 110 further includes a reference data unit 115 that is connected to the control unit 107 and that is configured to receive and/or generate and/or store reference data, also referred to as a calibration library, that characterizes the pitch calibration standard 111. In one embodiment, the reference data unit 115 may be configured as a storage unit to which, internally or externally, generated reference data is supplied and stored. In other embodiments, the reference data unit may comprise a calculation section to compute the reference data as required.

FIG. 1b schematically shows the scatterometry system 100 with the pitch calibration station 110 positioned to receive the light beam 102. It should be noted that the scatterometry system 100 may be provided in any appropriate configuration to supply a light beam to the pitch calibration station 110 and to detect the scattered light beam 104 with the detector 103. The examples in FIGS. 1a–1c are merely of an illustrative nature.

In FIG. 1c, further illustrative embodiments are schematically depicted in which the pitch calibration station 110 and/or the light source 101 and the detector 103 and/or the optical paths of the light beams 102 and 104 are altered such that the pitch calibration standard 111 may receive the light beam 102 and emit the light beam 104. As depicted in the plan view of FIG. 1c, in one embodiment, fixed reflective elements 120 and 121 and moveable reflective elements 122 and 123 may be provided, wherein the moveable reflective elements 122 and 123 may be translated along the direction as indicated by arrows 124. When the reflective elements 122 and 123 are in a position as depicted in FIG. 1c, the light beam 102 is deflected to the reflective element 120 and is directed to the pitch calibration standard 111. The fixed reflective element 121 is positioned to receive the reflected light beam 104 and to deflect it to the moveable reflective element 123 which, in turn, deflects the light beam 104 to the detector 103. When the moveable reflective elements 122 and 123 are removed from the optical path of the light source 101, the light beam 102 now impinges on the substrate holder 105 and on a substrate (not shown) mounted thereon. Moreover, a beam splitter (not shown) may be provided to split the light beam 102 into a first portion impinging on the substrate holder 105 and a second portion impinging on the pitch calibration standard 111. Actuating beam splitter block elements (not shown) may be provided to alternately supply, to the detector 103 the beam reflected by the substrate holder 105 and by the pitch calibration standard 111. Thus, the light beam "experiences" substantially identical conditions in the two measurement positions.

In a further embodiment, the reflective elements 120, 121, 122 and 123 are omitted and the light source 101 and the detector 103 are mounted on an appropriate drive assembly (not shown) so as to be moveable along the direction as indicated by arrows 125. In this way, alternately the pitch calibration standard 111 or the substrate holder 105 may receive the light beam 102.

In operation, the control unit 107 may cause the pitch calibration station 110 to be positioned so as to receive the light beam 102 emitted by the light source 101. A corresponding positioning of the pitch calibration station 110 may be carried out upon initializing the scatterometry system 100 and/or upon user request and/or a user-defined time interval has elapsed and/or a predefined number of measurements has been performed. Irrespective of when the pitch calibration station 110 is positioned to receive the light beam 102 or how this is accomplished, by moving the pitch calibration station 110 and/or the light source 101 and/or substrate holder 105 and/or by providing means for modifying an optical path, the pitch calibration standard 111 generates, upon incidence of the light beam 102, the reflected light beam 104 including information on the structure configuration of the pitch calibration standard 111.

It may be preferable to mount the pitch calibration standard 111 on the substrate stage 112 in such a way that substantially no additional orientation of the pitch calibration standard 111 is necessary prior to exposing it to the light beam 102. A corresponding arrangement significantly accelerates the measurement procedure, thereby allowing a large number of reference measurements without unduly affecting the measurement of product substrates. In other embodiments, the pitch calibration standard 111 may be appropriately oriented, for example, by means of the drive assembly 113, to correctly position the pitch calibration standard 111 with respect to the incident light beam 102. The light beam 102 is then scattered by the pitch calibration standard 111 to form the scattered light beam 104, the optical characteristics of which are, among others, determined by the properties of the pitch calibration standard 111. The detector 103 receives the light beam 104 and supplies the output signal 106 to the control unit 107, which, in turn, is connected to the reference data unit 115 including the reference data for the pitch calibration standard 111. The control unit 107 may, in one embodiment, be adapted to automatically compare the reference data with the information included in the output signal 106 to provide one or more measurement values, indicating one or more specified characteristics of the pitch calibration standard 111. For instance, the control unit 107 may output a measurement value indicating the pitch of the periodic pattern in the pitch calibration standard 111 so that the status of the scatterometry system 100 may be assessed on the basis of the actual and well-known pitch of the pitch calibration standard 111 and the measurement value obtained from the control unit 107. Since the pitch calibration standard 111 may be formed in such a manner that a variation of the properties of the pitch calibration standard 111 within a well-controlled environment, such as in a semiconductor process line, is negligible, any deviation of the well-known actual value from the obtained measurement value is an indication of a parameter drift of the scatterometry system 100. The scatterometry system 100 may only then be released for the measurement of product substrates when the measurement value obtained is within a predefined tolerance.

Figure 2:
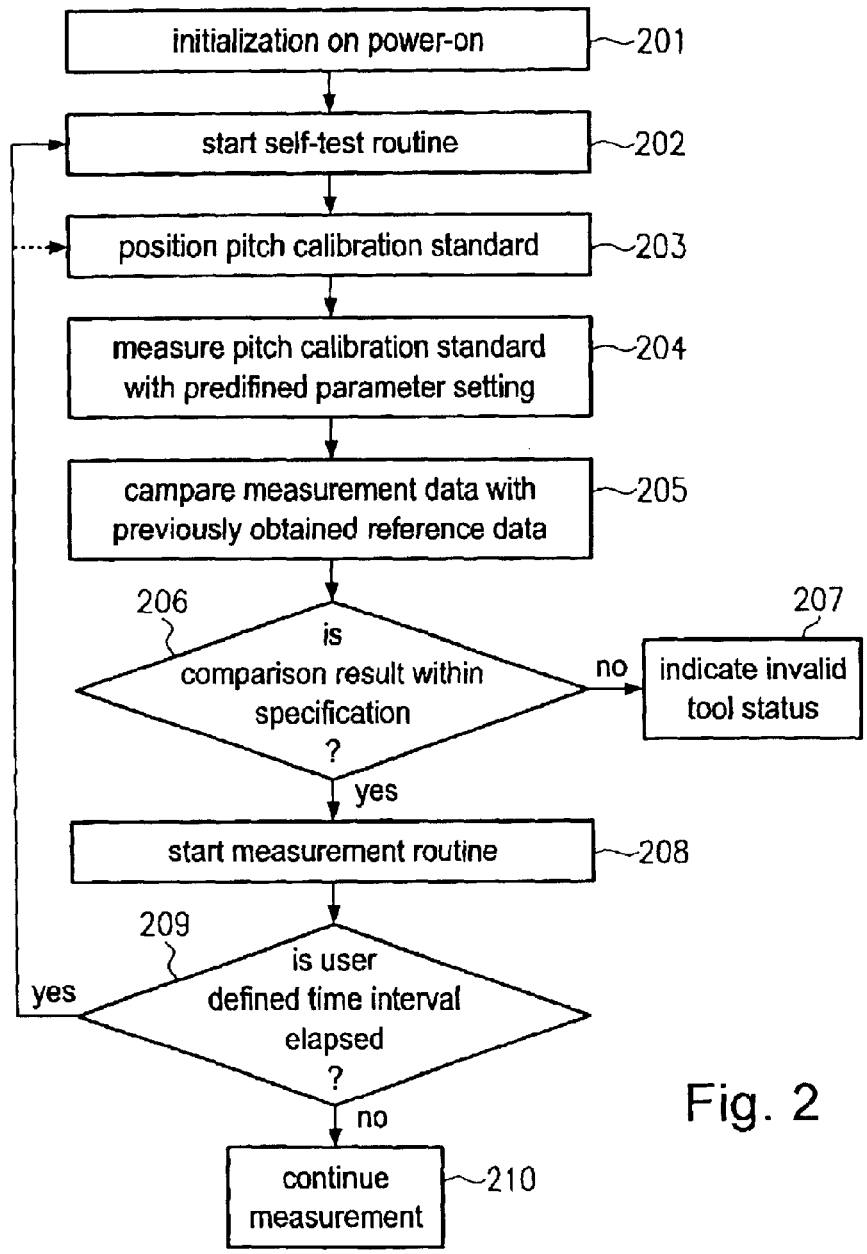
FIG. 2 is a flowchart depicting one particular embodiment for operating a scatterometry system as, for example, depicted in FIGS. 1a–1c.

With reference to FIG. 2, further illustrative embodiments of the present invention will now be described. In these embodiments, a self-test routine is implemented in the scatterometry system 100, for instance by providing an accordingly adapted control portion within the control unit 107, as is the case in already available metrology tools such as spectroscopic ellipsometers and photometers. In FIG. 2, in step 201, the scatterometry system 100 is initialized after turning on the device. In other embodiments, an initialization may be effected upon user request. In step 202, the self-test routine is started and various steps may be performed involved in establishing and verifying a certain predefined status of the scatterometry system 100. In step 203, which may be performed after, during or before any of the previously described steps, the pitch calibration standard 111 is appropriately positioned to receive the light beam 102. As previously explained, any type of positioning method may be applied in accordance with the scatterometry system's capabilities. In step 204, the pitch calibration standard 111 is measured with a predefined parameter setting that may be defined in advance or may be selected during the self-test routine. The predefined parameter setting may include specified values for the wavelength(s) of the light beam 102, the polarization state thereof, angle of incidence, position of the detector 103, and the like. In step 205, the measurement data obtained is compared to the reference data provided by the reference data unit 115, wherein preferably the reference data has previously been established and stored in the reference data unit 115 prior to starting the self-test routine. In other embodiments, however, the reference data may be established interactively, possibly on the basis of the parameter setting used in step 204. As previously noted, preferably the design of the pitch calibration standard 111 is as simple as possible so as to facilitate the establishment of reference data and to allow a quick and easy verification of dominant parameters of the scatterometry system 100. In step 206, it is assessed whether the comparison result of step 205 is within a specified value range and, when the comparison result does not meet the specification, in step 207, an invalid device status is indicated. When the result of the comparison yields a value within the specification, in step 208, the scatterometry system 100 is released and the measurement routine for product substrates may be started.

In one embodiment, the measurement routine includes, in step 209, a query, whether a user-defined time interval is elapsed and/or whether a predefined number of products has been measured and/or an external request for a calibration measurement has been received, and the process flow continues the measurement routine, as indicated in step 210, when the result of step 209 yields that the user-defined time interval has not yet elapsed and/or the predefined number of substrates has not yet been processed and/or an external request has not been received. If, however, the query in step 209 yields a "yes," the process flow returns to step 202 to restart the self-test routine. In another embodiment, for a "yes" in step 209, the process flow branches to step 203 to immediately begin the calibration measurement without further self-test checks. In this way, the status of the scatterometry system 100 is monitored on a regular basis, wherein the time intervals between the various status checks may be selected in conformity with process requirements.

Figure 3:
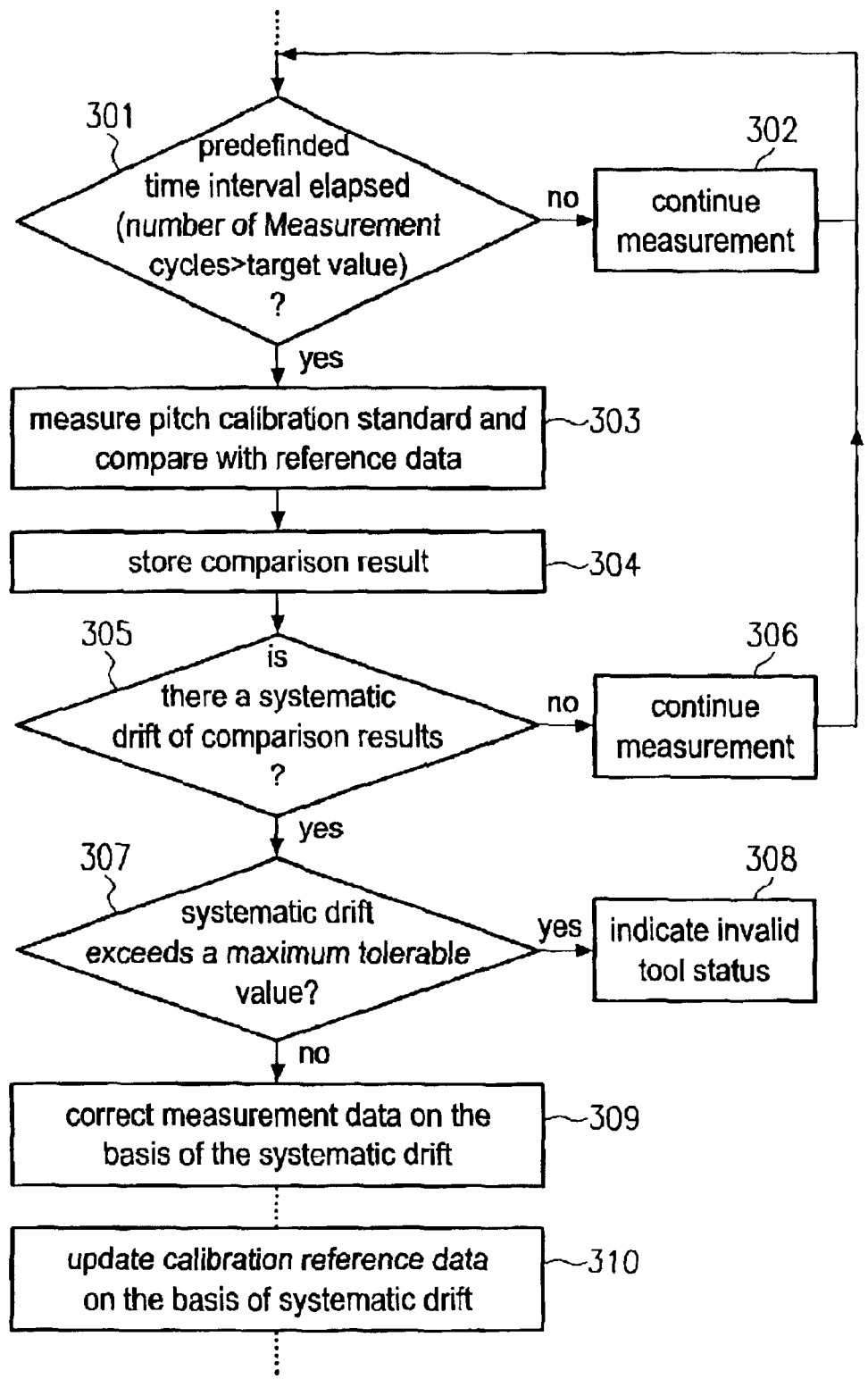
FIG. 3 is another flowchart depicting an operation mode of a further illustrative embodiment of the present invention.

With reference to the flowchart of FIG. 3, further illustrative embodiments of the present invention will now be described. According to the process flow depicted in FIG. 3, a measurement process may have taken place prior to step 301 in which it is assessed whether a predefined time interval has elapsed and/or a number of measurement cycles is reached. In case the criteria are not met, according to step 302, normal measurement procedure is continued. If the criteria of step 301 are met, the process flow branches to step 303, in which the pitch calibration standard 111 is measured and compared with corresponding reference data. Regarding the measurement procedure and the comparison with reference data, the same criteria apply as explained previously. Then, in step 304, the results of the comparison of step 303 are stored, for example, in a storage section in control unit 107 or in a corresponding portion of the reference data unit 115 or in any other appropriate storage means (not shown). In step 305, it is then assessed whether there is a systematic drift of the comparison results, on the basis of the results obtained in step 304 and on the basis of previously obtained comparison results. In one embodiment, the assessment may include the determination of an averaged value of the comparison results previously obtained, for example, in the form of a weighted moving average, in which, depending on the requirements, an appropriate weighting factor or weighting procedure may be used. For example, in one embodiment, a so-called exponentially weighted moving average may be calculated to estimate the degree of parameter drift of the scatterometry system 100. When the parameter drift is assessed, in step 305, to be within a tolerable range, the process flow branches to step 306 to continue the ordinary measurement procedure. In one embodiment, if the parameter drift is assessed to be outside of a tolerable range in step 305, an invalid tool status may be indicated and the measurement procedure is discontinued.

According to a further illustrative embodiment, if a systematic drift is recognized in step 305, the process flow may branch to step 307 in which the amount of drift is quantified and, upon exceeding a maximum tolerable value, the process flow branches to step 308 in which an invalid tool status is indicated and the measurement is discontinued. If, however, step 307 reveals a systematic drift that does not require discontinuation of the measurement procedure, the process flow branches to step 309, in which one or more correction values may be established to correspondingly correct measurement data. In one embodiment, the scatterometry system 100 may be configured to store at least a limited number of previously obtained measurement data so that, on the basis of the one or more correction values established in step 309, the measurement data of previously processed substrates may be corrected. Moreover, the one or more correction values may be used for substrates to be measured before the next measurement of the pitch calibration standard takes place in step 303. Instead of or additionally to establishing the one or more correction values in step 309, the process flow may advance to step 310 in which the reference data stored in the reference data unit 115 are updated on the basis of the systematic drift determined in step 307. If the reference data unit 115 interactively establishes the reference data, the corresponding computation may be carried out on the basis of the comparison results. In this way, a sort of "self consistent" calibration method may be established, in which reference data of the pitch calibration standard are steadily updated and adapted to the current tool status. Consequently, by storing the comparison results of measurements of the pitch calibration standard 111 in step 304, the "tool history" may be continuously monitored and thus, due to the substantially constant properties of the pitch calibration standard 111, allows the assessment of tool stability and measurement process quality. Advantageously, the average value and/or the standard deviation of the stored results of the calibration measurement may be used to "quantify" the tool history so that the long-term stability of the scatterometry system 100 may be expressed by a single number. In particular, the tool history allows extraction of valuable diagnosis information in situations of tool failures that may be caused by hardware and/or software errors.

It should be pointed out that the illustrative embodiments described above are, of course, completely or in parts exchangeable with each other so that one or more process steps, described with reference to FIG. 3, may be implemented as well into the process flow, described with reference to FIG. 2. In particular, storing the comparison results of the pitch calibration standard measurements may advantageously be implemented into a corresponding self-test routine as described in the illustrative embodiments of FIG. 2.

As a result, the pitch calibration station of the present invention allows automatic monitoring of the tool status of a scatterometry system and automatic indication of an invalid tool status. Thus, due to the traceability of the pitch calibration standard, the accuracy and trustworthiness of measurement results of the scatterometry system may significantly be improved.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A scatterometry system comprising:
   a light source configured to emit a light beam of predefined optical characteristics;
   a detector configured to receive a light beam and output a signal indicative of optical characteristics of the received light beam;
   a substrate holder configured to receive and position a substrate so as to receive the light beam from said light source and scatter a portion of the light beam to said detector; and
   a pitch calibration station including a pitch calibration standard to provide measurement data indicative of the current system status.

2. The scatterometry system of claim 1, further comprising a reference data unit to provide reference data describing the pitch calibration standard.

3. The scatterometry system of claim 2, wherein the reference data unit comprises a storage unit to receive and store the reference data.

4. The scatterometry system of claim 1, further comprising a beam positioning assembly configured to alternatively position said pitch calibration standard and said substrate holder so as to receive the light beam emitted by said light source.

5. The scatterometry system of claim 4, wherein the beam positioning assembly comprises a drive assembly coupled to said substrate holder and said pitch calibration station.

6. The scatterometry system of claim 4, wherein the beam positioning assembly comprises a drive assembly configured to move said light source and said detector to alternatively provide a light beam emitted by the light source to said pitch calibration standard and the substrate holder.

7. The scatterometry system of claim 3, wherein the beam positioning assembly comprises a plurality of reflective elements arranged to alternatively direct the light beam emitted by the light source to the pitch calibration standard and the substrate holder.

8. The scatterometry system of claim 7, wherein one or more of said reflective elements are moveable.

9. The scatterometry system of claim 1, wherein said pitch calibration standard comprises a grating structure.

10. The scatterometry system of claim 1, further comprising a storage unit configured to store a measurement data obtained from said pitch calibration station.

11. A method of monitoring a status of a scatterometry system, the method comprising:
    providing a pitch calibration standard;
    establishing a reference data library for said pitch calibration standard;
    obtaining measurement data of said pitch calibration standard; and
    comparing said measurement data with said reference data library to assess the status of the scatterometry system.

12. The method of claim 11, wherein obtaining measurement data of said pitch calibration standard is carried out upon occurrence of at least one of the following situations:
    an initialization of the scatterometry system, an elapse of a predefined time interval, a completion of a predefined number of measurement cycles and an external request for a calibration measurement.

13. The method of claim 11, wherein obtaining measurement data and comparing said measurement data with the reference data library is carried out during a self-test routine of the scatterometry system.

14. The method of claim 11, wherein comparing the measurement data with the reference data library includes assessing whether a difference of the reference data and the measurement data is within a predefined allowable range.

15. The method of claim 14, further comprising indicating an invalid tool status when said difference is outside of said predefined allowable range.

16. The method of claim 14, further comprising storing a value indicative of said difference to establish a tool history.

17. The method of claim 11, wherein said light source, said detector and said substrate holder are provided in the form of one of an ellipsometer and a photometer.

18. The method of claim 11, wherein said pitch calibration standard is a grid pattern.

19. The method of claim 16, wherein establishing said tool history includes determining at least one of an average value and a standard deviation of a plurality of values indicative of differences between measurement data and the reference data library of previously performed measurements with said pitch calibration standard.

20. The method of claim 19, wherein said reference data library is updated on the basis of the tool history.

21. The method of claim 16, wherein one or more correction values are established on the basis of the tool history.

22. A method of operating a scatterometer, the method comprising:
    starting a self-test routine of the scatterometer, the self-test routine including:
        obtaining measurement data from a pitch calibration standard;
        comparing said measurement data with reference data characterizing the pitch calibration standard; and
        indicating that the scatterometer is acceptable for performing measurements when a result of said comparison is within a predefined allowable range.

23. The method of claim 22, wherein said self-test routine is started upon occurrence of at least one of the following events:
    an initialization of the scatterometer, an external request, an elapse of a predefined time interval and a completion of a predefined number of measurement cycles.

24. The method of claim 22, further comprising storing said comparison result to establish a tool history.

25. The method of claim 24, further comprising updating said reference data on the basis of the tool history.

26. The method of claim 25, further comprising measuring a substrate and evaluating measurement data of said substrate on the basis of substrate reference data and said tool history.

27. The method of claim 22, further comprising indicating an invalid tool status when said comparison result is outside of a predefined allowable range.

* * * * *